(12) United States Patent
Kolody et al.

(10) Patent No.: US 7,020,917 B1
(45) Date of Patent: Apr. 4, 2006

(54) RADIOLUCENT SURGICAL TABLE WITH LOW SHADOW ACCESSORY INTERFACE PROFILE

(75) Inventors: Timothy Kolody, Lorain, OH (US); Ward L. Sanders, Albion, PA (US); Victor M. Selig, Euclid, OH (US)

(73) Assignee: Steris Corporation, Mentor, OH (US)

( * ) Notice: Subject to any disclaimer, the term of this patent is extended or adjusted under 35 U.S.C. 154(b) by 5 days.

(21) Appl. No.: 09/804,287

(22) Filed: Mar. 12, 2001

(51) Int. Cl.
*A61G 13/10* (2006.01)
*A61B 5/05* (2006.01)

(52) U.S. Cl. .................. 5/621; 5/601; 108/28; 378/209

(58) Field of Classification Search ..................... 5/601, 5/600, 621–624, 730, 7, 31; 248/227.2, 227.1; 403/55, 59; 108/27, 28, 32, 50.11; 24/457; 378/208, 209

See application file for complete search history.

(56) References Cited

U.S. PATENT DOCUMENTS

| | | | |
|---|---|---|---|
| 2,212,156 A | 8/1940 | Erdley | |
| 3,046,072 A | 7/1962 | Douglass Jr. et al. | |
| 3,339,913 A | 9/1967 | Anderson | |
| 3,386,444 A | 6/1968 | Brenner et al. | |
| D221,910 S | 9/1971 | Brendgord | |
| 3,627,250 A * | 12/1971 | Pegrum | 248/324 |
| 3,981,492 A | 9/1976 | Hallmann | |
| 4,018,412 A | 4/1977 | Kees, Jr. et al. | |
| 4,043,278 A * | 8/1977 | Kessler et al. | 108/150 |
| 4,069,813 A | 1/1978 | Gilula | |
| 4,122,587 A | 10/1978 | Weiss et al. | |
| 4,143,652 A | 3/1979 | Meier et al. | |
| 4,145,612 A | 3/1979 | Cooper | |
| 4,146,793 A | 3/1979 | Bergstrom et al. | |
| 4,221,371 A | 9/1980 | Kuphal | |
| 4,287,422 A | 9/1981 | Kuphal et al. | |
| 4,346,298 A | 8/1982 | Dixit | |
| 4,355,631 A | 10/1982 | LeVahn | |
| 4,484,571 A * | 11/1984 | Velazquez | 5/601 |
| 4,487,523 A | 12/1984 | Monroe | |
| 4,506,872 A * | 3/1985 | Westerberg et al. | 5/601 |
| 4,547,092 A | 10/1985 | Vetter et al. | |
| D287,625 S | 1/1987 | Brendgord et al. | |
| 4,698,837 A | 10/1987 | Van Steenburg | |
| 4,796,846 A | 1/1989 | Meier et al. | |
| 4,805,202 A | 2/1989 | Deucher et al. | |
| 4,828,208 A * | 5/1989 | Peterson et al. | 248/188.2 |
| 4,901,964 A | 2/1990 | McConnell | |
| 4,926,457 A * | 5/1990 | Poehner et al. | 378/208 |

(Continued)

*Primary Examiner*—Jack W. Lavinder
(74) *Attorney, Agent, or Firm*—Fay, Sharpe, Fagan, Minnich & McKee, LLP (57) ABSTRACT

A radiolucent surgical table (40) is provided with a low shadow accessory interface profile (70). The interface profile includes a plurality of interconnected curved surfaces formed along the entire outer edge of the patient support member for selective attachment to a range of medical accessory devices. The support interface includes a non-planar first connection area (72) having a recess (82) and a curved lip area (90) adapted to engage correspondingly formed surfaces (122, 126) on a medical accessory connector (110, 140). A second connection area (76) of the support interface (70) includes a planar locating surface (100) formed at an angle oblique with the top surface (74) of the patient support member. Engagement with the locating surface by corresponding surfaces formed on the medical accessory connectors (110, 140) generate a downward force that causes an increase in the engagement forces between the recess and lip areas of the interface and corresponding surfaces on the accessory connectors.

30 Claims, 7 Drawing Sheets

U.S. PATENT DOCUMENTS

| | | |
|---|---|---|
| 4,936,836 A | 6/1990 | Weickgenannt |
| 4,971,037 A | 11/1990 | Pelta |
| 5,014,969 A | 5/1991 | Schaefer |
| 5,029,826 A | 7/1991 | Schaefer |
| 5,077,780 A * | 12/1991 | Lee, Jr. ................. 378/196 |
| 5,078,705 A | 1/1992 | Edwards et al. |
| 5,090,044 A | 2/1992 | Kobayashi |
| 5,097,132 A | 3/1992 | Plummer |
| 5,099,550 A * | 3/1992 | Beane et al. ................. 24/555 |
| 5,131,103 A * | 7/1992 | Thomas et al. ................. 5/601 |
| 5,201,088 A * | 4/1993 | Larsson ................. 474/150 |
| 5,276,927 A * | 1/1994 | Day ................. 5/601 |
| 5,279,603 A | 1/1994 | Everett et al. |
| 5,287,575 A | 2/1994 | Allen et al. |
| 5,337,760 A | 8/1994 | Nichols |
| 5,400,772 A * | 3/1995 | LeVahn et al. ................. 600/230 |
| 5,535,973 A | 7/1996 | Bailey et al. |
| 5,538,215 A | 7/1996 | Hosey |
| 5,581,830 A | 12/1996 | Schwieker |
| 5,613,254 A | 3/1997 | Clayman et al. |
| 5,628,853 A * | 5/1997 | Edwards ................. 156/212 |
| 5,701,991 A | 12/1997 | Helmetsie |
| 5,754,997 A * | 5/1998 | Lussi et al. ................. 5/601 |
| 5,771,513 A | 6/1998 | Kirchgeorg et al. |
| D408,537 S | 4/1999 | Stickley et al. |
| 5,983,426 A * | 11/1999 | Vanek et al. ................. 5/621 |
| 6,023,800 A | 2/2000 | Stickley |
| 6,260,220 B1 * | 7/2001 | Lamb et al. ................. 5/601 |
| 6,671,904 B1 * | 1/2004 | Easterling ................. 5/601 |

* cited by examiner

RADIOLUCENT SURGICAL TABLE WITH LOW SHADOW ACCESSORY INTERFACE PROFILE

BACKGROUND OF THE INVENTION

1. Field of the Invention

The present invention relates to radiolucent surgical tables and, more particularly, to a radiolucent surgical table with a low radiographic shadow edge profile used to support a patient adjacent x-ray imaging devices such as C-arm scanners, CT, fluoroscopic, and other whole body scanners.

2. Description of the Prior Art

Conventional surgical tables include a flat patient support and a lower base for holding the patient support a predetermined distance from the floor. The base of conventional surgical tables commonly includes control apparatus for tilting the flat patient support through a range of orientations to facilitate performance of certain surgical procedures. Typical flat patient supports are made of surgical stainless steel and in most cases include a set of metal side rails supported along the edges of the table for holding surgical accessories, instrumentation, and the like. Typically, the side rails conform to an industry standard cross sectional size and configuration so that surgical accessories from any vendor source can be directly connected to surgical tables built by another vendor without modification of the attachment interface.

One disadvantage of stainless steel table tops of the type described above is that they block x-rays. Accordingly, their use in surgical or interventional procedures that require x-rays, fluoroscopic or other patient images to be taken are quite limited.

As a result, patient support tables have been proposed that utilize an x-ray translucent material, such as phenolic resins, in selected portions of the table top. The x-ray translucent material allows interoperative x-ray image signals to be generated using fluoroscopic devices, C-arm or CT scanners and other imaging equipment.

Figure 1:
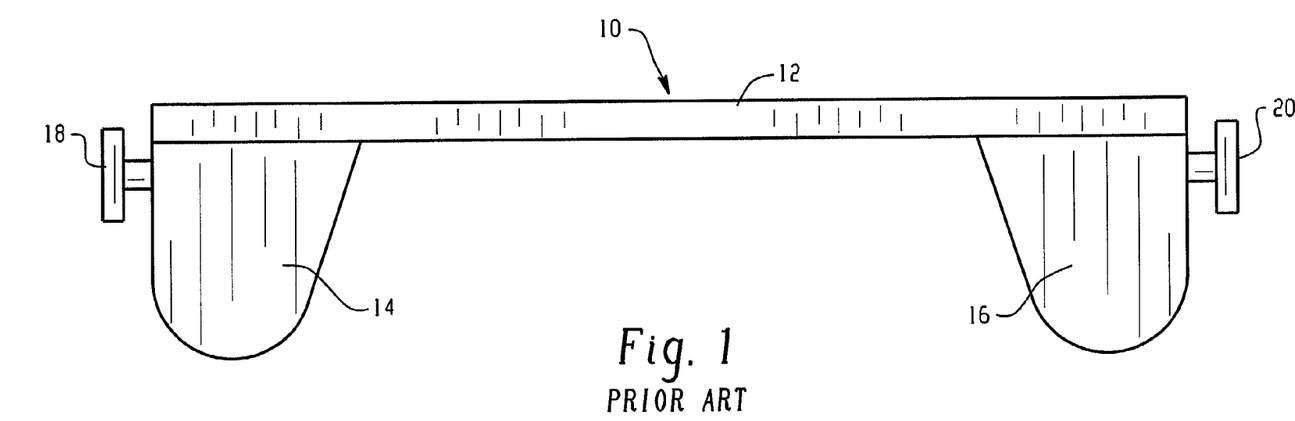
FIG. 1 is a cross-sectional view of a prior art radiolucent surgical table taken along a line (not shown) extending in a direction transverse to the table.

One such example of a prior art radiolucent table is shown at FIG. 1. As illustrated in cross section, the flat patient support 10 includes a substantially planar table top member 12 formed of a x-ray translucent material such as, for example, a carbon fiber material or a phenolic resin such as sold under the tradename SPAULDITE. Due mainly to load carrying capacity limitations and to enhance stiffness, the table top 12 is supported on either side by a pair of longitudinally extending metal frame members 14, 16. Each of the metal frame members 14, 16 are attached to the bottom surface of the table top member 12 using a suitable cement such as an epoxy, fasteners, or the like. A pair of side rail members 18, 20 are held in a fixed relationship relative to the metal frame members 14, 16 as illustrated. The side rail members 18, 20 have a size and shape that conform to the industry-wide standards noted above.

One disadvantage of the flat patient support 10 illustrated in FIG. 1 is that the metal frame members 14, 16 as well as the side rail members 18, 20 generate shadows when the patient support 10 is used in radiographic imaging procedures. As a result, only the portion of the radiopaque table top member 12 that is disposed between the pair of metal frame members 14, 16 is usable for radiographic imaging. This limitation becomes more pronounced when the table is tilted relative to the x-ray generator. The angle of the table relative to the x-ray source effectively shortens the distance between the metal side frame members 14, 16 as viewed from the x-ray source thus reducing the shadow-free areas in the radiographic image.

Figure 2:
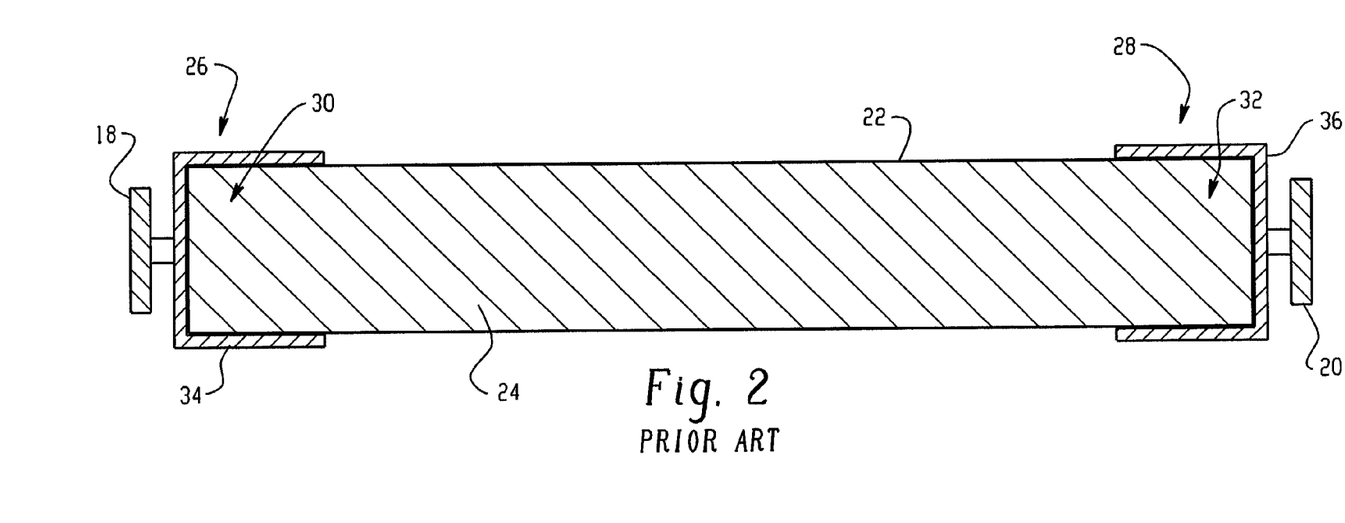
FIG. 2 is a cross-sectional view of a prior art radiolucent surgical table taken along a line (not shown) extending in a direction transverse to the surgical table.

FIG. 2 illustrates another prior art surgical table configuration that is somewhat useful in radiographic imaging and in certain interventional procedures. As shown there, a predominant feature of the flat patient support 22 is a relatively thick slab 24 of radiographic material having a generally rectangular cross section. The slab 24 is provided on opposite transverse edges 26, 28 with a substantially square accessory interface profile 30, 32 as shown. Each of the accessory interface profiles 30, 32 are sized and shaped to receive a pair of accessory coupler members 34, 36 on the opposite transverse edges 26, 28 of the radiolucent slab 24. In turn, each coupler member 34, 36 carries an industry standard side rail member 18, 20 of the type described above. In that way, most commercially available accessories can be used with the table.

One drawback to the "slab" type radiolucent surgical tables shown in FIG. 2 is that the accessory coupler members 34, 36 are typically formed of metal and therefore obstruct x-ray signal propagation through portions of the table along the table edges. As a result, undesirable shadows are formed in the radiographic image.

Simple removal of the accessory coupler members 34 or 36 does not completely solve the shadow problem. The vertical surfaces along the square edges of the accessory interface profiles 30, 32 lead to shadows in radiographic images. The shadows are caused because, during normal use of the table, the vertical edges of the profile are typically aligned in a substantially parallel relationship with x-ray signal propagation. As a result, the edge surfaces tend to attenuate the x-ray signal to a substantial degree greater than the flat horizontal surfaces and, accordingly, the vertical edge surfaces generate shadows in the radiographic image.

It is, therefore, desirable to provide a radiolucent surgical table that presents a substantially uniform attenuation characteristic to x-ray signals in both the lateral and transverse directions and with the table held flat or tilted relative to the x-ray signal source. In that way, the radiographic images of a patient disposed on such surgical table would be free and clear of extraneous shadows.

It is further desirable to provide such a table that, in addition to being substantially x-ray shadow free, provides a surgical accessory interface profile so that a wide range of surgical accessories can be easily and directly connected anywhere along the edge of the table top. Preferably, the accessory interface profile presents a substantially uniform attenuation characteristic to x-rays passing through the table top and table top edges regardless of the angle of the table top relative to the x-ray source.

SUMMARY OF THE INVENTION

In accordance with the present invention, therefore, a shadow free radiolucent patient support table is provided including substantially planar top and bottom surfaces held apart in an opposed relationship. The radiolucent patient support table is preferably formed of an outer layer of carbon fibers surrounding an inner foam core. The outer longitudinal edges of the support table define a substantially continuous medical appliance support interface for selectively connecting a plurality of associated medical appliances to the table. The medical appliance support interface generally comprises a non-planar first connection area defined on the top surface of the surgical table and a second connection area defined on the side of the table top. The non-planar first connection area is shaped to provide first and second static supporting forces against an associated medical appliance, when connected to the table, in directions substantially parallel to and perpendicular with the top and bottom surfaces of the table. The second connection area is shaped to provide third and fourth static supporting forces against the associated medical appliance in third and fourth directions substantially parallel to and perpendicular with the top and bottom surfaces. The first and third forces cooperate to support a load moment generated by the medical accessory held by the table edge. The second and fourth forces cooperate to support the medical accessory against gravity and in a vertical direction.

In accordance with one aspect of the invention, the non-planar first connection area includes a curved lip surface extending along the upper edge of the table top and at least one recess defined between a pair of wall surfaces that converge at a bight region of the at least one recess. The lip and recess are preferably formed as a continuous smoothly curved surfaces disposed along the outer longitudinal edges of the table top.

In accordance with yet another aspect of the invention, the second connection area includes a substantially planar surface held at an oblique angle relative to the substantially planar top and bottom surfaces. The planar surface of the second connection area forms an acute angle with the top surface of the table and forms an obtuse angle with the bottom surface of the table. In that way, the second connection area generates a static counter-force against the associated medical appliance connector in a downward direction relative to the table top so that a downwardly directed lip formed on the connector is forced into tight engagement with the at least one recess defined by the first connection area.

In accordance with a still further aspect of the present invention, a segmented medical appliance connector is provided for attaching a wide range of surgical accessories directly to the table top at selected positions along the interface profile. The connector includes movable upper and lower jaws that are adapted to clamp onto the interface profile.

In accordance with still yet a further aspect of the invention, a unitary appliance connector is provided for attaching surgical accessories to the table top. The unitary connector includes a resilient engagement area that is adapted to be press-fitted onto the interface profile of the table top. The unitary connector has no moving parts and therefore is easy to use and can be sterilized conveniently.

It is a primary object of the invention to provide a radiolucent surgical table that presents a substantially uniform attenuation characteristic over the entire surface area of the table top in both lateral and transverse table top directions with the table held flat or tilted relative to the x-ray source.

It is another object of the invention to provide such a table top that includes an accessory interface profile along the edge of the table top so that various surgical accessories, instruments, and the like can be quickly and easily attached to the radiolucent table as needed. The accessory interface edge profile presents a substantially uniform x-ray attenuation characteristic because it is formed without flat surfaces in alignment with the x-ray propagation direction. Essentially all of the surfaces of the interface edge profile are curved, rounded, or flat and disposed at oblique angles relative to the x-ray propagation direction.

It is another object of the invention to provide a radiolucent surgical table with a low shadow accessory interface profile that is convertible for use in a wide range of surgical and interventional procedures by providing a set of intermateable table top portions that are selectively arranged and fastened together into various configurations as needed. Preferably, the table top portions are connected using simple pin type attachment mechanisms.

It is yet another object of the invention to provide medical appliance connectors that are adapted to cooperate with the interface profile defined in the surgical table top to support various surgical devices and instruments relative to the table.

These and other objects and benefits of the present invention will be described below.

BRIEF DESCRIPTION OF THE DRAWINGS

The invention may take physical form in certain parts and arrangements of parts, the preferred embodiments of which will be described in detail in this specification and illustrated in the accompanying drawings which form a part hereof, and wherein.

DETAILED DESCRIPTION OF THE PREFERRED EMBODIMENTS

Figure 3:
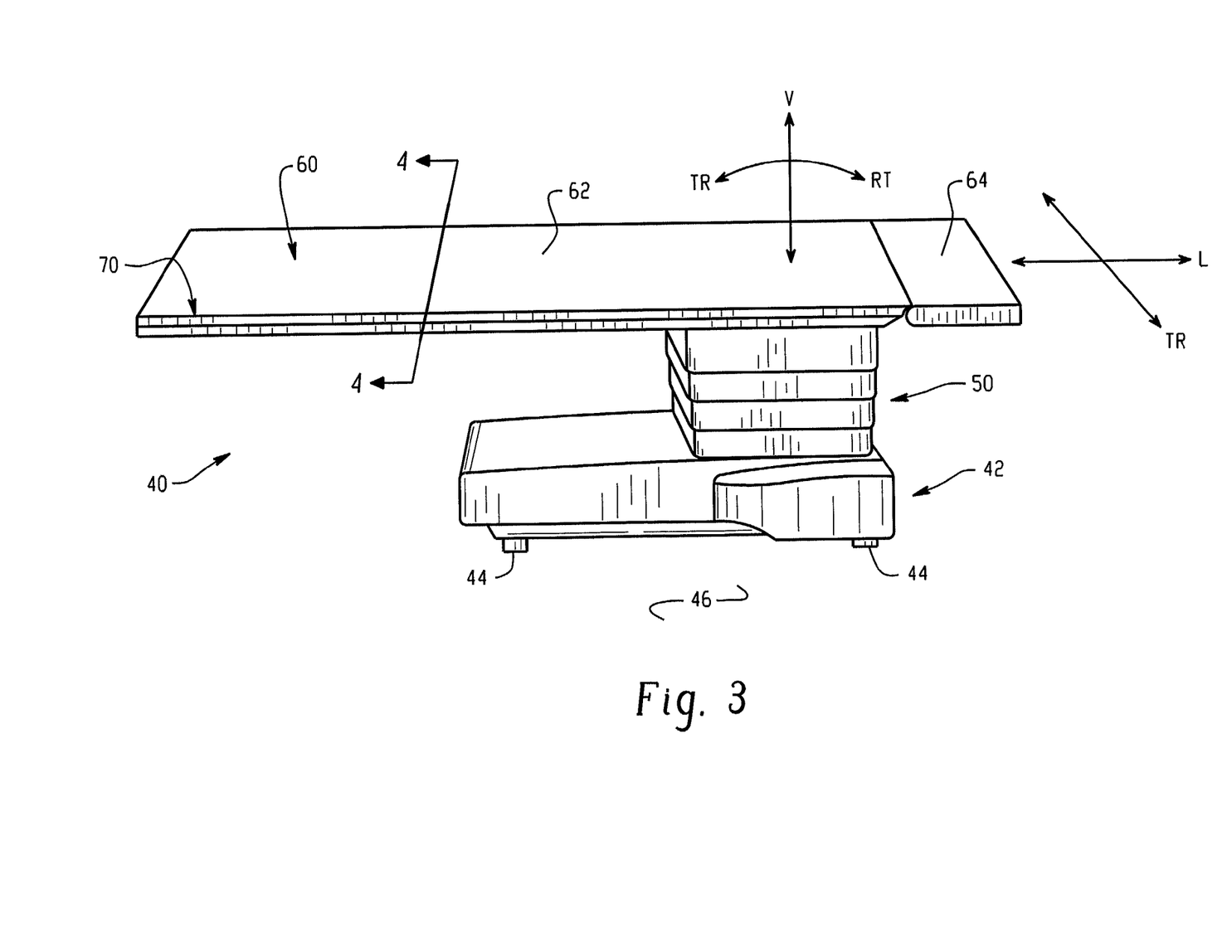
FIG. 3 is an isometric view showing the subject radiographic surgical table in accordance with a first preferred embodiment supported on a mobile base.

Referring now to the drawings wherein the showings are for the purposes of illustrating the preferred embodiments of the invention only and not for purposes of limiting same, FIG. 3 illustrates a floor mounted surgical table 40 with a radiolucent patient support member 60 and medical appliance support interface 70 formed in accordance with a first preferred embodiment of the invention. The table 40 has a somewhat conventional base section including a base member 42 which is supported by four legs 44, one leg 44 disposed at each corner of base member 42. The legs 44 may be of the retractable type which can be withdrawn into the base member 42 to permit wheels (not shown) to contact floor 46 and enable hospital personnel to conveniently reposition the surgical table 40 within a room. A vertical support and positioning column 50 is secured on a first lower end to the base member 42. The second or upper end of the column 50 supports the substantially planar radiolucent patient support member 60 in selected positions relative to the base member 42. The column 50 preferably includes control mechanisms and operators well known in the art for tilting the control housing together with the radiolucent patient support member 60 into various orientations relative to the base member 42 to facilitate performance of a wide variety of surgical, interventional, and imaging procedures. A basic raise and lower function is provided within the column 50 to enable the patient support member 60 to be moved vertically relative to the base member 42 as shown in FIG. 3 at arrow V. Additionally, a tilt function is provided within the column to enable the patient support member 60 to be pivoted relative to the base member 42. In that way, the support member 60 can be moved into Trendelenburg positions as shown in FIG. 3 at arrow TR and reverse-Trendelenburg positions as shown at arrow RT.

Still further, the upper end of the column 50 preferably includes a X-Y translation mechanism (not shown) for enabling sliding movement between the radiolucent patient support member 60 and the column 50. A basic rail and bearing system of the type commonly used in industrial applications is preferably used. Systems of this type are available to provide smooth, accurate, and repeatable positioning between the respective members throughout the range of translation movement. In the present invention, longitudinal translation of the patient support member 60 in the direction L is provided relative to the column 50 over a range of travel of about twenty-four inches (24"). Transverse translation of the patient support member 60 in the direction T relative to the column 50 is provided over a range of travel of about twelve inches (12"). Although x-y translation of the table 60 relative to the column 50 is preferred, in an alternative embodiment, the table is immovable in the x-y plane relative to the column 50.

As shown in FIG. 3, the radiolucent patient support member 60 of the first preferred embodiment is essentially formed as a monolithic single slab construction including a major body and leg support section 62 connected to the column 50 and a smaller headrest section 64 pivotally attached with the body and leg support section 62. The sections are constructed of a foam core surrounded with outer layers of carbon fibers. Preferably, the headrest section 64 is selectively lockable in positions throughout a range of pivotal motion relative to the main body section 62. This allows the patient's head to be supported in raised or lowered positions as desired.

With continued reference to FIG. 3, the longitudinal edges of the radiolucent patient support member 60 form a medical appliance support interface 70 for selective connection of associated appliances to the table 40.

Preferably, the support interface 70 is formed to extend continuously around each outer longitudinal and transverse edges of the support member 60 including the body and leg support section 62 and the headrest section 64 as shown best in FIG. 3. A noted above, the support interface 70 adapts the outer edges of the surgical table 40 to selectively receive a wide variety of associated surgical accessory devices. Thus, by providing the support interface 70 along the outer edges of the table top in a manner as shown in FIG. 3, the associated surgical appliances can be conveniently located anywhere along the sides of the surgical table 40 including positions on either side of a patient and adjacent the head and feet of the patient.

Figure 4:
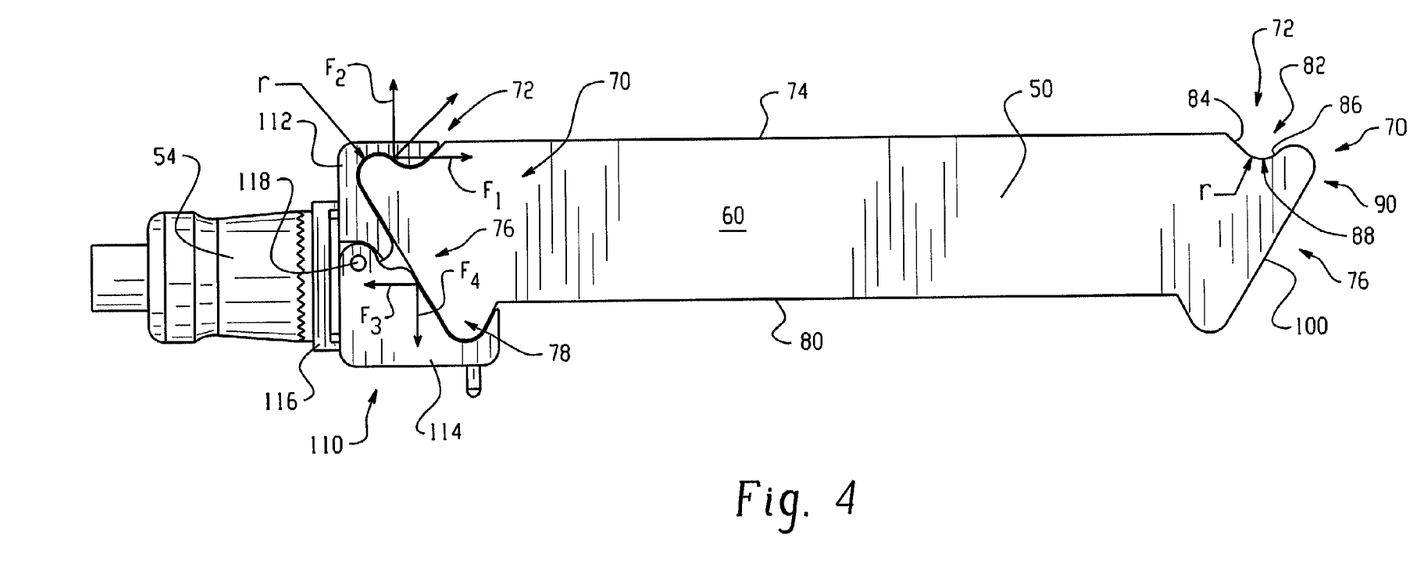
FIG. 4 is a cross-sectional view taken generally on line 4—4 of FIG. 3 and showing a segmented medical accessory attached thereto.

With continued reference to FIG. 3, and with additional reference to FIG. 4, the subject medical appliance support interface 70 includes a non-planar first connection area 72 defined on the top surface 74 of the radiolucent patient support member 60. In addition, the support interface 70 includes a second connection area 76 that is defined on the outer edge of the radiolucent patient support member 60 in a manner as shown. A non-planar third connection area 78 is defined at the bottom outer edge of the patient support member 60. The first 72 and second 76 connection areas support an associated medical appliance 54 relative to the table against gravity and normal downward loading. The second 76 and third 78 connection areas support the medical appliance relative to the table against upward loading such as may be experienced when the appliance is a medical restraint or the like.

FIG. 4 shows, in cross section, the preferred shape of the subject accessory interface 70 and the manner in which the interface is used to selectively connect various associated medical appliances 54 to the patient support member 60. With particular reference now to that figure, the non-planar first connection area 72 is shaped to provide a first support force $F_1$ against an associated medical appliance 54 in a first direction substantially parallel to the top and bottom surfaces 74, 80 of the patient support member 60. Further, the first connection area 72 is shaped to provide a second supporting force $F_2$ against the associated medical appliance 54 in a second direction substantially perpendicular to the top and bottom surfaces 74, 80, respectively.

The second connection area 76 is defined generally on the edge of the patient support member 60 as shown to provide a third supporting force $F_3$ against the associated medical appliance 54 in a third direction substantially parallel to the top and bottom surfaces 74, 80 of the support member. The second connection area 76 is formed to also provide a fourth supporting force $F_4$ against the associated medical appliance 54 in a fourth direction substantially perpendicular to the top and bottom surfaces 74, 80.

As can be seen from the figure, the first and second connection areas 72, 76 cooperate to support the medical appliance relative to the table against gravity and normal downward loading. The static forces $F_1$–$F_4$ combine to provide the necessary resultant forces to support the associated medical appliance. The third connection area 78 is necessary only when upward loading is expected to be encountered.

Preferably, and in accordance with the present invention, the first connection area 72 includes at least one recess 82 defined between a pair of concave wall surfaces 84, 86 that converge at bight area 88 as shown. Essentially, the bight area 88 is formed in the valley between the pair of opposed concave wall surfaces 84, 86. Preferably, the bight area 88 is a continuous rounded surface formed between the opposed concave wall surfaces 84, 86 as shown. This configuration enables x-ray signals to pass through the first connection area 72 of the support interface 70 along a transmission path substantially perpendicular to the top and bottom surfaces 74, 80 without encountering surfaces parallel with the transmission path. Surfaces parallel with the transmission path as well as surfaces that are close to parallel with the transmission path absorb the x-ray signal to a larger degree than surfaces which are oblique or perpendicular to the x-ray path. Accordingly, by forming the first connection area 72 without surfaces parallel or close to parallel with the x-ray transmission path, the first connection area 72 enables a substantially shadow-free image along the outer edge of the radiolucent patient support member 60.

It is to be appreciated that the bight area 88 could include a flat surface between the opposed concave wall surfaces 84, 86 and parallel with the top and bottom surfaces 74, 80 of the support member 60 without adversely affecting x-ray signal propagation through the first connection area 72. This enables an elongated first connection area if desired. In that case, the upward supporting force $F_2$ would be spread out over a larger (wider as viewed in the figure) surface area.

The outer wall surface 86 is somewhat shorter than the inner wall surface 84 relative to the top surface 74 of the radiolucent patient support member 60 so that various medical accessories can be attached to the support member without extending above the plane defined by the top surface 74. In that way, the upper portion of the medical accessory connector essentially forms a planar extension of the table top surface 74. Alternatively, the outer wall surface 86 can be formed to be the same size as or larger than the inner wall surface 84 relative to the top surface 74 of the patient support member 60. In those equivalent structures, the upper portion of the associated medical accessory connector would extend above the plane defined by the top surface 74 when the connector is disposed in the clamped-on position relative to the support interface 70.

With continued reference to FIG. 4, the outer wall surface 84 extends outwardly relative to the center of the patient support member to form a downwardly curved lip area 90 as shown. Preferably, in accordance with the present invention, the curved lip area 90 as well as the recess 82 are substantially circular in cross section and are curved to define a first radius r. The curved lip area as well as the recess are preferably formed without interruption or breaks along the entire outer longitudinal edges of the radiolucent patient support member 60 as best shown in FIG. 3.

As is apparent from the cross sectional view of the patient support member 60 shown in FIG. 4, the first connection area 72 provides a convenient surface for hanging medical devices and other equipment on the edge of the surgical table. In order to provide precise mechanical locating of the associated medical devices relative to the table top, the second connection area 76 is formed to define a substantially planar locating surface 100 that is preferably disposed at an angle oblique to the top and bottom surfaces 74, 80 of the support member 60. Preferably, the locating surface 100 forms an angle of approximately 50 degrees relative to the top surface 74. In this configuration, the locating surface 100 provides an undercut in the patient support member 60 that is advantageously used to multiply the load moment generated by the associated medical accessory into a clamping force between the recess and curved lip area 82, 90 and a downwardly directed portion of a connector assembly fashioned to engage the recess and curved lip area.

In that regard and with attention now directed to the left portion of the cross sectional view shown in FIG. 4, a segmented medical accessory connector 110 is illustrated in tight mechanical engagement with the medical appliance support interface 70. As shown, the segmented connector 110 includes movable upper and lower jaw members 112, 114 that are carried on a main body portion 116 of the accessory connector. Preferably, in accordance with the present invention, the jaw members 112, 114 are pivotally connected to the main body portion 116 at a pivot joint 118. In that way, the jaws can be opened so that the accessory connector can be selectively attached onto the medical appliance support interface 70.

Figure 5A:
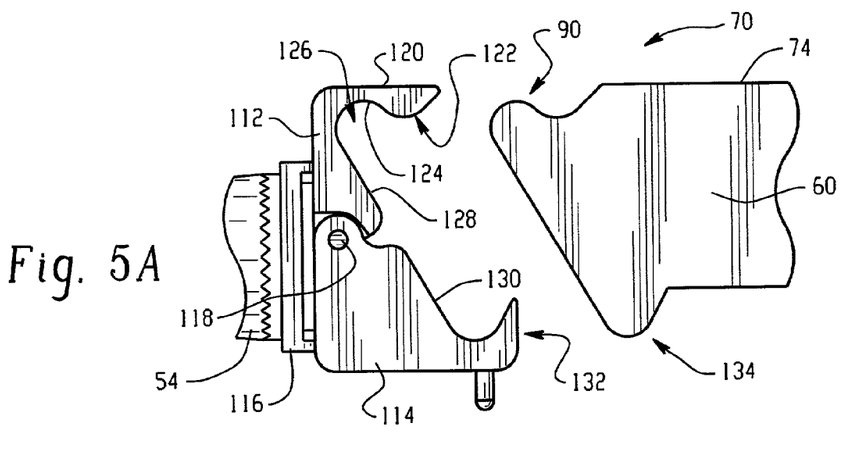
FIGS. 5A–5C illustrate a sequence of steps for connecting a segmented medical accessory connector onto the radiolucent table top.
Figure 5B:
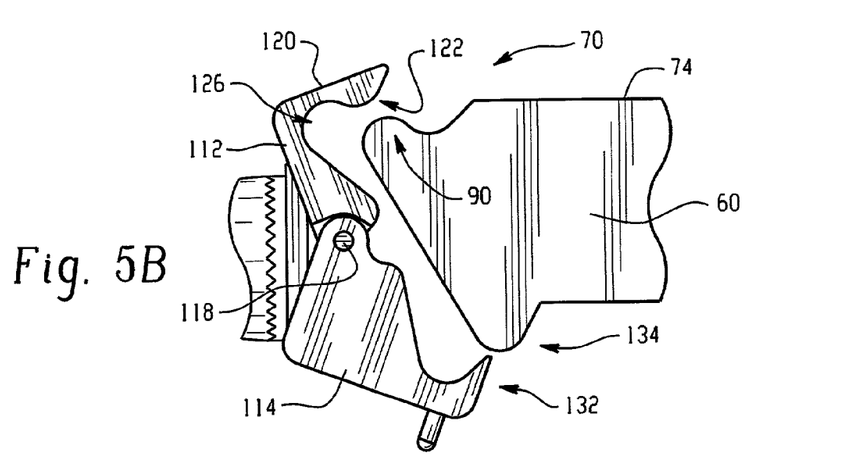
Figure 5C:
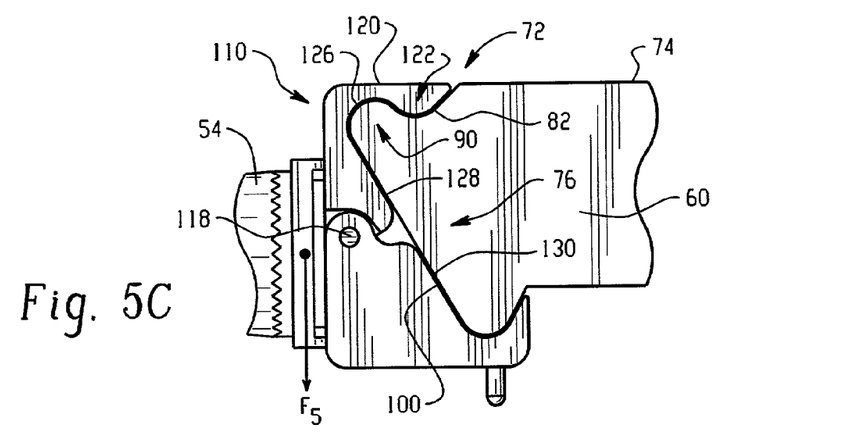

FIGS. 5A–5C illustrate the preferred manner in which the segmented medical accessory connector 110 is attached to the medical appliance support interface 70. Turning now to those figures, the medical accessory connector 110 is first brought in general relative alignment with the medical appliance support interface 70 as shown best in FIG. 5A. It is to be noted that preferably, the movable upper jaw member 112 includes a substantially planar top surface 120 that forms, in the connected position, an extension to the radiolucent patient support member 60 substantially within the plane of the top surface 74 thereof. Further, the movable upper jaw member 112 includes a downwardly projecting lip 122 and a curved concave surface 124 that defines a pocket 126 adapted to receive the curved lip area 90 of the support interface 70. Lastly, the movable upper jaw member 112 includes a substantially planar upper engagement surface 128 that is coextensive with a lower engagement surface 130 defined by the lower jaw member 114 when the accessory connector 110 is disposed in a closed orientation as shown in FIG. 5A.

Turning now to FIG. 5B, the subject segmented medical accessory connector 110 is shown in its opened position whereat the upper and lower jaw members 112, 114 are rotated relative to the pivot connection 118 into the positions shown for ready attachment onto the medical appliance support interface 70. The upper jaw member 112 is pivoted upwardly to an extent to enable the downwardly projecting lip 122 to pass freely over the curved lip area 90 of the support interface 70. In a similar fashion, the lower movable jaw member 114 is pivoted downwardly to an extent to enable a hook region 132 of the lower jaw member to pass freely over a flared edge 134 of the third connection area 78 of the radiolucent patient support member 60. Preferably, in accordance with the present invention, the movable upper and lower jaw members are biased into the closed position illustrated in FIGS. 5A and 5C and are brought into the opened orientation for ready attachment onto the support interface when the jaws are simultaneously held open by mechanical means such as by manual manipulation.

FIG. 5C illustrates the segmented medical accessory connector 110 in its operative closed position and clamped onto the patient support member 60 via the appliance support interface in accordance with the present invention. As shown, the movable upper jaw member 112 is securely seated against the first and second connection areas 72, 76. The movable lower jaw member 114 is similarly securely seated against the second and third connection areas 76, 78. In that regard, the downwardly projecting lip 122 of the upper jaw member 112 is held in place within the recess 82 of the support interface 70 through engagement with the concave wall surfaces 84, 86. Further, the pocket 126 formed on the underside of the upper jaw member 112 is securely held in place through mechanical engagement with the curved outer surface of the lip area 90 formed on the outer edge of the patient support member 60. The upper and lower engagement surfaces 128, 130 are brought into planar engagement with the locating surface 100 formed as an undercut on the patient support member 60. In that way, a downward force $F_5$ generated by the associated medical appliance 54 attached to the accessory 110 generates a torque moment centered about the curved lip area 90. The force of the torque moment is converted by the planar interface between the locating surface 100 and the upper and lower engagement areas 128, 130 into a downward force that is utilized to ensure snug engagement between the downwardly projecting lip 122 and pocket 126 of the upper jaw member 112 against the lip area and recess 90, 80 of the support interface.

Figure 6A:
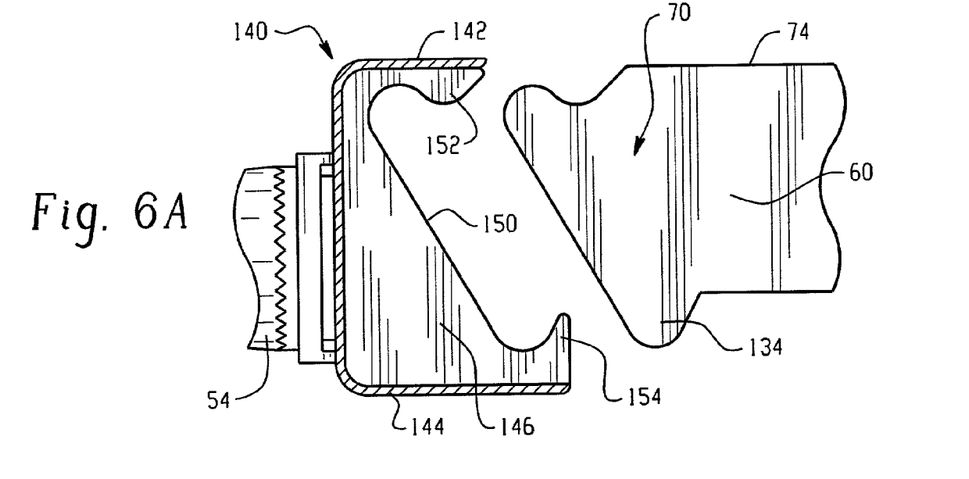
FIGS. 6A–6C show a sequence of steps for connecting a unitary medical appliance connector onto the subject radiolucent table top.
Figure 6B:
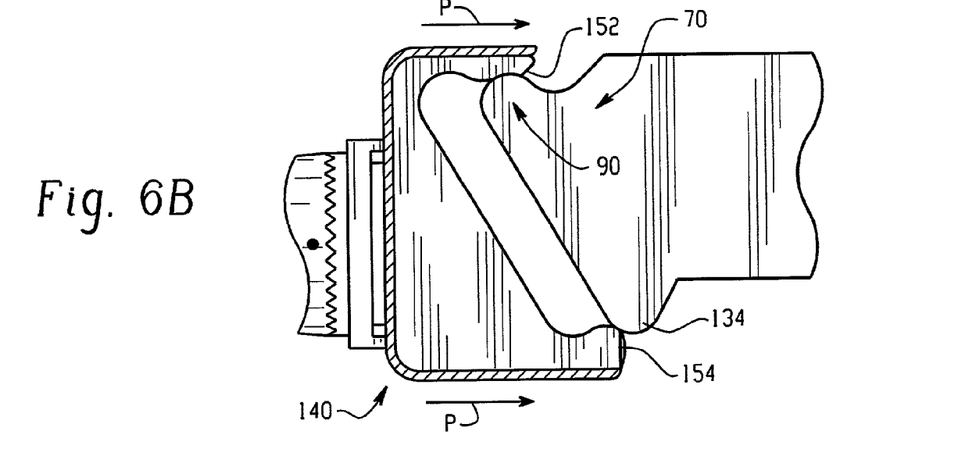
Figure 6C:
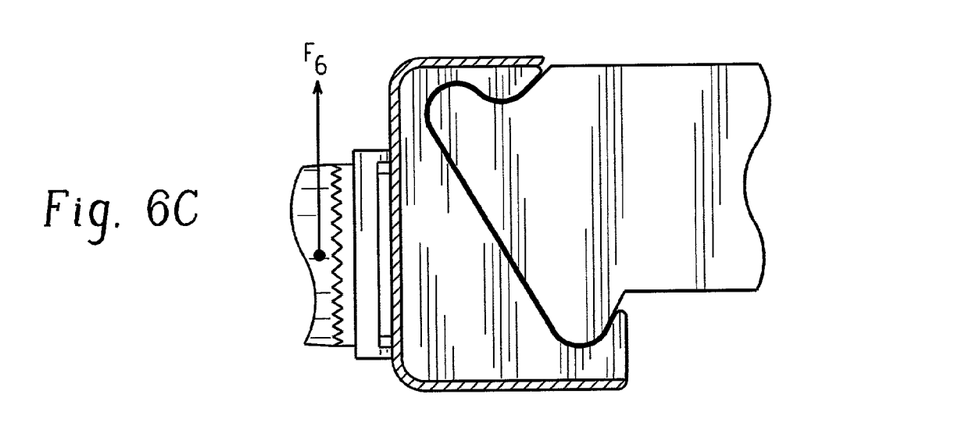

FIGS. 6A–6C illustrate the subject medical appliance support interface 70 used in conjunction with a substantially unitary medical accessory connector 140 that can provide both upward and downward forces against the interface. As shown first in FIG. 6A, the connector 140 is illustrated in operative position adjacent the support interface whereat a substantially planar top surface 142 of the accessory connector is brought into relative alignment with the top surface 74 of the support member 60. Preferably, the top surface 142 is formed by the upper portion of an outer C-shaped frame member 144 that is adapted to carry a resilient deformable holding element 146 as shown. Preferably, as illustrated, the holding element 146 has an outer surface 150 that is shaped as the mirror image of the outer surface of the medical appliance support interface 70. In that way, the unitary medical accessory connector 140 can be brought into intermated connection with the support interface 70 by simply pushing the accessory connector 140 onto the interface 70 against the force of the resilient deformable holding element 146 and into the position illustrated in FIG. 6C.

FIG. 6B illustrates the unitary medical accessory connector 140 midway between fully detached and attached positions. As illustrated, a downwardly projecting lip member 152 is compressed by the lip area 90 of the support interface 70. Similarly, the lower hook region 154 of the deformable holding element 146 is compressed by the lower flared edge 134 of the support interface 70. The unitary medical accessory connector 140 is brought into the final connected position illustrated in FIG. 6C by moving the connector relative to the patient support member 60 in the direction marked P in FIG. 6B. The unitary connector is snap-fitted into place simply by using a force adequate to overcome the friction and compressive force on the resilient deformable holding element 146. Preferably, the holding element 146 is formed of any suitable resilient elastomeric material such as a stiff rubber material or the like.

Similar to the above discussion in connection with the segmented medical accessory connector 110, the unitary connector 140 illustrated in FIGS. 6A–6C includes a lower hook region 154 that is adapted to surroundingly engage the flared edge 134 of the third connection area 78 disposed at the lower outer edge of the support member 60. The engagement between the hook region and the flared edge helps prevent detachment of the unitary medical accessory connector 140 from the support interface 70 when the medical appliance 54 attached thereto is subjected to an upward oriented disrupting force $F_6$.

Figure 7:
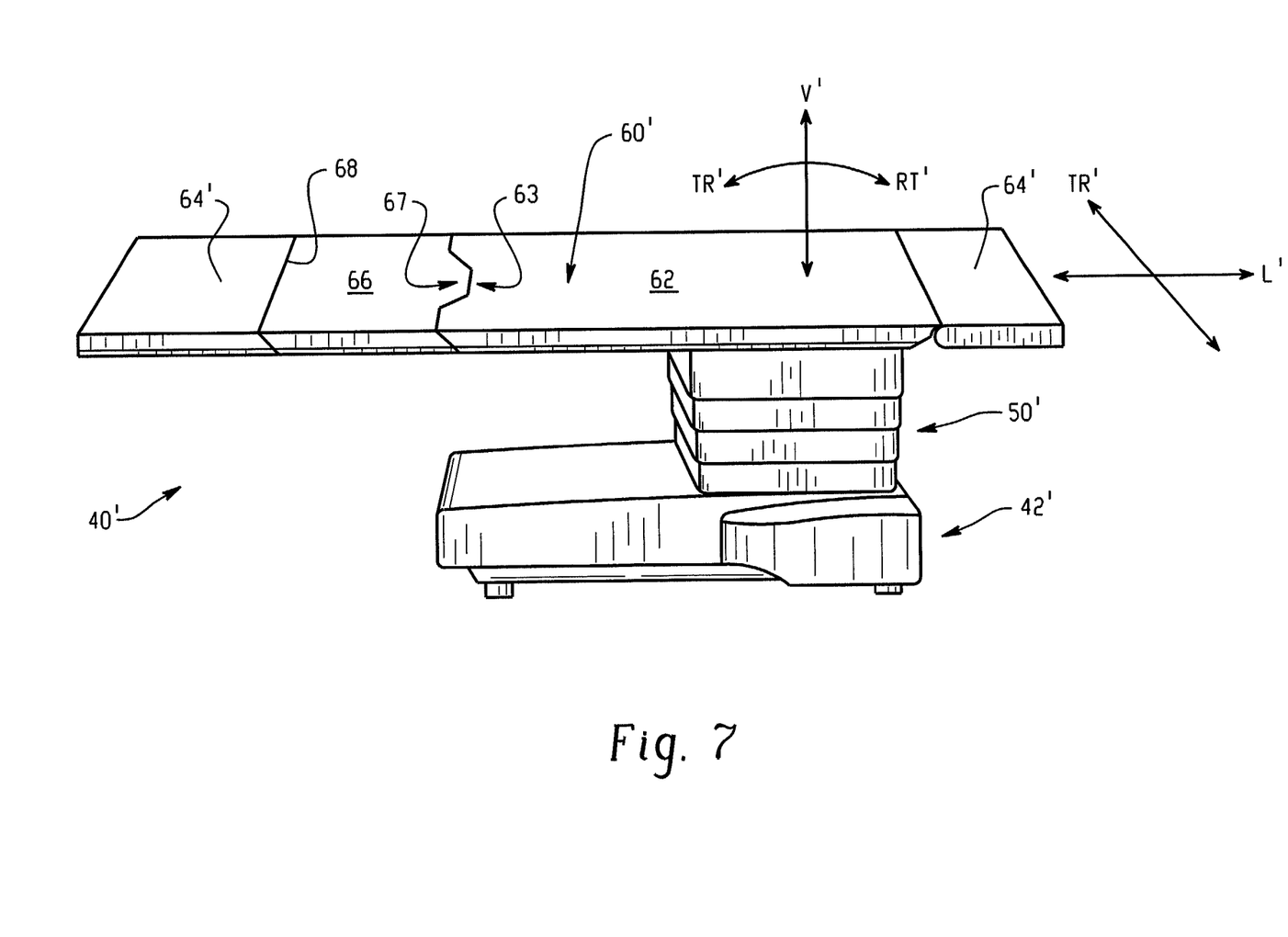
FIG. 7 is an isometric view showing the subject radiolucent table in accordance with a second preferred embodiment; and, FIG. 8 is an isometric view showing the subject radiolucent medical surgical table supported by a vertical support column in accordance with a third preferred embodiment of the invention.

FIG. 7 is an isometric view showing the subject radiolucent table in accordance with a second preferred embodiment. As illustrated there, the table 40' has a conventional base section including a base member 42' and a vertical support and positioning column 50'. The column 50' is secured on a first lower end to the base member 42' and preferably includes control mechanisms and operators well known in the art for tilting the control housing together with the radiolucent patient support member 60' into various orientations relative to the base member 42' to facilitate performance of a wide range of surgical, interventional, and imaging procedures. A base raise and lower function is provided within the column 50' to enable the patient support member 60' to be moved vertically relative to the base member 42' as shown in FIG. 7 at arrow V'. Additionally, tilt functions are provided within the column 50' to enable the patient support member 60' to be pivoted relative to the base member 42' in Trendelenburg and reverse-Trendelenburg positions as shown at arrows T' and RT', respectively.

Still further, the upper end of the column 50' includes an x-y translation mechanism (not shown) for enabling sliding movement between the radiolucent patient support member 60' and the column 50'.

Of particular relevance to the second preferred embodiment of the invention, the radiolucent patient support member 60' is segmented in a manner to facilitate a plurality of medical procedures which have heretofore required specialized tables for each procedure. In the embodiment illustrated in FIG. 7, the patient support member 60' includes a major body support section 62' connected to the upper end of the column 50' substantially as shown. A cardio-vascular extender member 66 includes a trapezoidal connection region 67 for interengagement with a correspondingly reverse-shaped trapezoidal region 63 provided in the body support section 62'. The cardiovascular extender member 66 and major body support section 62' are selectively connected using suitable pin and lock type fasteners extending horizontally outwardly from the foam core at the trapezoidal connection edges.

In one preferred embodiment, the cardiovascular extender member 66 has an overall length of about twenty inches (20"). This length together with a suitable attachment edge 68 for connection to a smaller headrest section 64' pivotally attached to the extender member 66 enables a wide range of thoracic surgeries to be performed on a patient such as, for example, heart and lung operations.

In another embodiment, the cardiovascular extender member 66 has an overall length of approximately twenty-two inches (22") for supporting the hips and legs of a patient lying upon the table in a "normal" orientation. The smaller headrest section 64' is pivotally attached to the major body support section 62' in a manner described above in connection with FIG. 3. The second preferred embodiment illustrated in FIG. 7 enables the use of a cardiovascular extender member 66' of selected lengths to be used to help facilitate certain surgical procedures. Furthermore, the second preferred embodiment illustrated in FIG. 7 enables the headrest section 64' to be attached to either the major body support section 62' or to the cardiovascular extender member 66' as desired.

Figure 8:
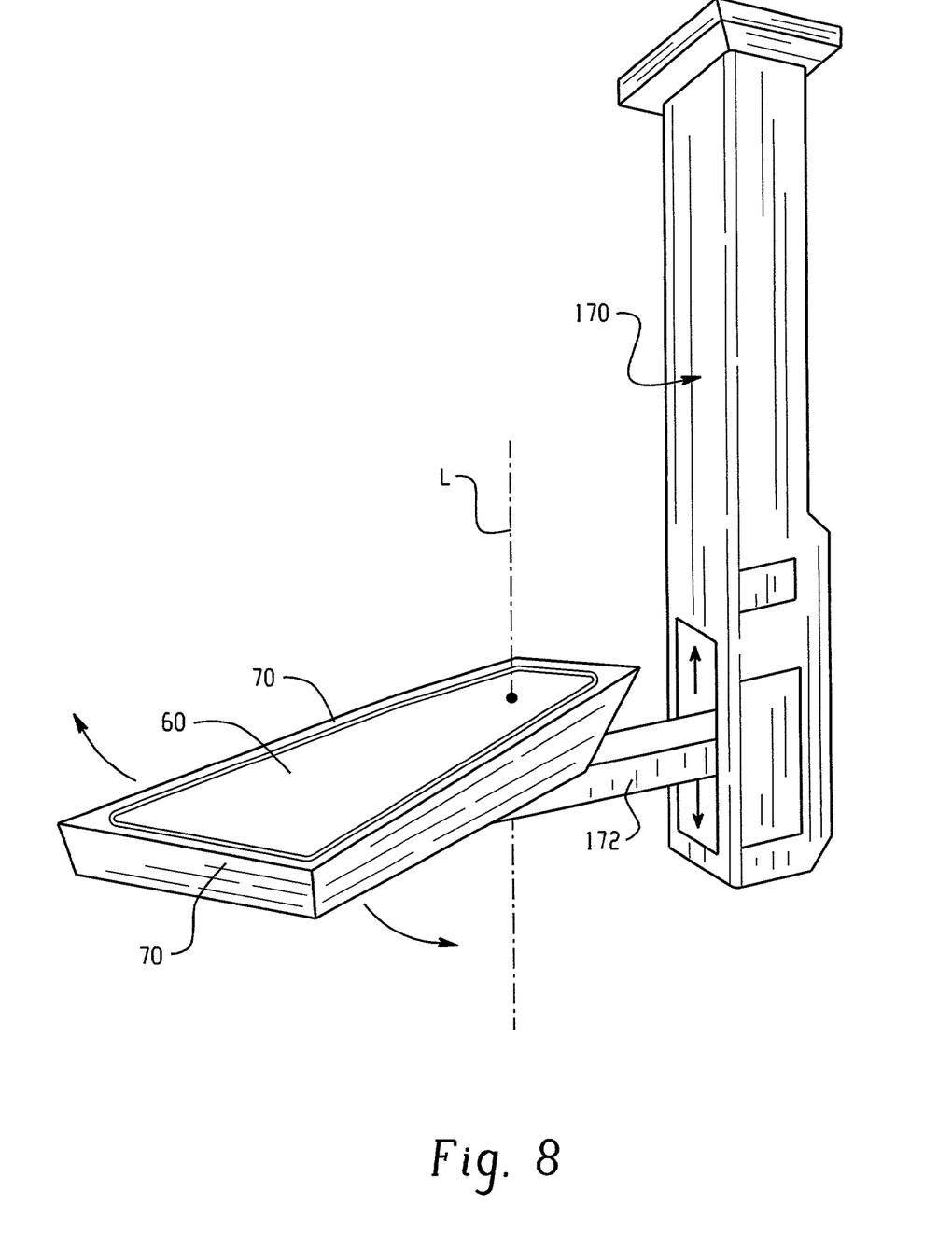

Turning lastly now to FIG. 8, the subject medical appliance support interface 70 is shown in conjunction with a radiolucent patient support member 60 that is supported by a vertical column member 170 extending between a ceiling and floor of a medical procedure room. In this embodiment, the patient support member 70 is connected to the vertical column 170 using a horizontally oriented support bar 172. The support bar is vertically movable within the support column 170 to enable positioning of the support members 60 relative to the floor so that the height of the patient relative to equipment disposed on the floor can be easily modified. In addition, the horizontal support bar 172 preferably enables rotatable motion so that the patient support member can be tilted, inclined, or declined as necessary. Lastly, it is preferable that the patient support member 60 is attached to the horizontal support bar 172 using a rotatable connector so that the patient support member 60 can be rotated about an axis L for ease of patient access.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. In a radiolucent patient support table including substantially planar top and bottom surfaces held apart in an opposed relationship, a medical appliance support interface for selectively connecting an associated medical appliance to the table, the interface comprising:

a non-planar first connection area defined by a first portion of said top surface of the support table, the first connection area being shaped to provide a first supporting force against an associated medical appliance in a first direction substantially parallel to the top and bottom surfaces, and a second supporting force against the associated medical appliance in a second direction substantially perpendicular to the top and bottom surfaces, wherein said first connection area includes at least one recess defined between a pair of wall surfaces that converge at a bight of the at least one recess;

a second connection area defined by a second portion of said table and shaped to provide a third supporting force against the associated medical appliance in a third direction substantially parallel to the top and bottom surfaces, and a fourth supporting force against the associated medical appliance in a fourth direction substantially perpendicular to the top and bottom surfaces, wherein said second connection area includes a substantially planar surface held at an oblique angle relative to said substantially planar top and bottom surfaces; and, a rounded lip area formed between said at least one recess and said substantially planar surface, the rounded lip area defining a crest located between said bight and a plane defined by the top surface of the patient support table.

2. The medical appliance support interface according to claim 1 wherein said rounded lip area is spaced apart from the plane defined by the top surface by a predetermined distance.

3. A surgical table comprising:
a base member;
a column connected with the base member;
a rectangular radiolucent patient support member carried on the column, the patient support member defining substantially planar top and bottom surfaces; and,
a low radiographic shadow accessory connection interface defined by a plurality of curved surfaces of the patient support member along at least one edge of the patient support member for selectively connecting an associated accessory to the patient support member, the plurality of curved surfaces being without planar portions oriented in a substantially perpendicular relation to said planar top surface of the patient support member so that first portions of an associated x-ray signal passing through the connection interface along a path substantially perpendicular to the planar top surface are attenuated substantially the same as second portions of the x-ray signal passing through the patient support member.

4. The surgical table according to claim 3 wherein said plurality of curved surfaces of the low shadow connection interface includes a first connection area adjacent the planar top surface of the patient support member and a second connection area extending between the first connection area and the bottom surface of the patient support member, the first connection area including a curved lip surface and the second connection area including a planar locating surface disposed in a non-perpendicular relation with said planar top surface.

5. The surgical table according to claim 4 wherein the first connection area includes a curved recess surface formed in said planar top surface of the patient support member adjacent said curved lip surface.

6. The surgical table according to claim 5 wherein the curved recess surface formed in said planar top surface is defined by a pair of opposed spaced apart concave wall surfaces formed in the planar top surface of the patient support member adjacent said curved lip surface.

7. The surgical table according to claim 6 wherein:
the curved recess surface formed in the planar top surface defines a groove having a first radius r; and,
the curved lip surface defines a ridge having substantially said first radius r.

8. The surgical table according to claim 6 wherein the curved recess surface includes a planar intermediate surface extending between said spaced apart concave wall surfaces, the planar intermediate surface being substantially parallel with the planar top surface of the patient support member.

9. The surgical table according to claim 4 wherein the planar locating surface extends at an angle of about 50 relative to the top and bottom surfaces of the patient support member.

10. The surgical table according to claim 4 wherein:
the top surface of the patient support member defines a first plane; and,
the curved lip surface is disposed entirely on a side of said first plane containing said patient support member.

11. The surgical table according to claim 4 further comprising:
a third connection area between said second connection and said bottom surface of the patent support member, the third connection area including a downwardly directed curved ridge extending from the bottom surface of the patient support member in a direction opposite from said curved lip surface of said first connection area.

12. The surgical table according to claim 4 wherein the rectangular radiolucent patient support member includes a plurality of selectively intermateable support member portions including a body and leg support section connected with said column, a headrest section pivotally attached with the body and leg support sections, and a cardiovascular extender member selectively attachable to the body and leg support section.

13. The surgical table according to claim 4 wherein the column includes:
a vertical column member suspended from overhead by a ceiling of an associated surgical room; and,
a generally horizontally oriented support bar for pivotally connecting the patient support member with the vertical column member, the support bar being vertically movable relative to the column member to enable positioning of the patient support member relative to a floor of the associated surgical room.

14. In a radiolucent patient support table including substantially flat top and bottom surfaces held apart in an opposed relationship, a medical appliance support interface for selectively connecting an associated medical appliance to the table, the interface comprising:
a curved first connection area defined by a first portion of said top surface of the support table, the first connection area being shaped to provide a first supporting force against an associated medical appliance in a first direction substantially parallel to the top and bottom surfaces, and a second supporting force against the associated medical appliance in a second direction substantially perpendicular to the top and bottom surfaces, wherein said first connection area includes at least one recess defined between a pair of wall surfaces that converge at a bight of the at least one recess;
a second connection area defined by a second portion of said table and shaped to provide a third supporting force against the associated medical appliance in a third direction substantially parallel to the top and bottom surfaces, and a fourth supporting force against the associated medical appliance in a fourth direction substantially perpendicular to the top and bottom surfaces, wherein said second connection area includes a substantially planar surface held at an oblique angle relative to said substantially planar top and bottom surfaces; and, a rounded lip area formed between said at least one recess and said substantially planar surface, the rounded lip area defining a crest located between said bight and a plane defined by the top surface of the patient support table.

15. A medical appliance interface in a patient support table for creating forces on an associated medical appliance to support the associated medical appliance relative to the table, the medical appliance interface comprising:

a table top having, on opposite sides of the table top, a substantially flat upper surface and a substantially flat lower surface;

a groove defined by a portion of said upper surface, the groove being spaced from an upper edge of the table top defined by said upper surface;

a ridge defined by a portion of said lower surface, the ridge being disposed at a lower edge of the table top defined by said lower surface and extending beyond said substantially flat lower surface; and, a substantially flat side surface extending between said upper edge of the table top and said lower edge of the table top, the upper, lower, and side surfaces together with said groove and said ridge creating forces supporting the associated medical appliance relative to the table when the associated appliance is connected with the patient support table.

16. The medical appliance support interface according to claim 15 wherein said substantially flat side surface defines a beveled edge of said table top.

17. The medical appliance support interface according to claim 15 wherein the table top includes a foam core surrounded by an outer layer of carbon fibers.

18. The medical appliance support interface according to claim 15 wherein said substantially flat side surface is held at an oblique angle relative to at least one of said upper surface and said lower surface of said table top.

19. The medical appliance support interface according to claim 15 wherein:

said groove is an elongate groove extending substantially the length of said table top; and, said ridge is an elongate ridge extending substantially the length of said table top.

20. The medical appliance support interface according to claim 15 wherein the elongate groove is a recess defined between a pair of concave wall surfaces that converge at a bight area.

21. The medical appliance support interface according to claim 15 wherein said groove and said ridge are defined by exclusively curved surfaces.

22. The medical appliance support interface according to claim 15 wherein:

said flat upper surface of the table top defines a plane;

said groove formed by said portion of the upper surface is a recess defined between a pair of concave wall surfaces that converge at a bight area formed by said portion of the upper surface, the bight area being spaced apart from said plane defined by the upper surface; and, said upper edge of the table top terminates at a location between said bight area and said plane.

23. A medical appliance support interface for use with an associated radiolucent patient support table including substantially planar top and bottom surfaces held apart in an opposed relationship for selectively connecting an associated medical appliance with the table, the medical appliance support interface comprising:

a non-planar first connection area defined by the associated table, the first connection area being shaped to provide a first supporting force against the associated medical appliance in a first direction substantially parallel to the top and bottom surfaces, and a second supporting force against the associated medical appliance in a second direction substantially perpendicular to the top and bottom surfaces, wherein said first connection area includes at least one recess defined between a pair of wall surfaces that converge at a bight of the at least one recess;

a second connection area defined by the associated table and shaped to provide a third supporting force against the associated medical appliance in a third direction substantially parallel to the top and bottom surfaces, and a fourth supporting force against the associated medical appliance in a fourth direction substantially perpendicular to the top and bottom surfaces; and, a rounded lip area formed between said at least one recess and said substantially planar surface, the rounded lip area defining a crest located between said bight and a plane defined by the top surface of the patient support table.

24. The medical appliance support interface according to claim 23 wherein said rounded lip area is spaced apart from the plane defined by the top surface by a predetermined distance.

25. The medical appliance support interface according to claim 23 wherein said second connection area includes a substantially planar surface held at an oblique angle relative to said substantially planar top and bottom surfaces.

26. A surgical table comprising:

a base member;

a column connected with the base member;

a patient support member carried on the column, the patient support member including substantially planar top and bottom surfaces; and, an accessory connection interface defined by a plurality of curved surfaces of the patient support member along at least one edge of the patient support member for selectively connecting an associated accessory to the patient support member, the plurality of curved surfaces being without planar portions oriented in a substantially perpendicular relation to said planar top surface of the patent support member so that first portions of an associated x-ray signal passing through the connection interface along a path substantially perpendicular to the planar top surface are attenuated substantially the same as second portions of the x-ray signal passing through the patient support member.

27. The surgical table according to claim 26 wherein said plurality of curved surfaces of the accessory connection interface include a first connection area adjacent the planar top surface of the patient support member and a second connection area extending between the first connection area and the bottom surface of the patient support member, the first connection area including a curved lip surface and the second connection area including a planar locating surface disposed in a non-perpendicular relation with said planar top surface.

28. A surgical table comprising:
a base member;
a column connected with the base member;
a patient support member carried on the column, the patient support member including substantially planar top and bottom surfaces and a plurality of curved surfaces defining an accessory connection interface formed along at least one edge of the patient support member for selectively connecting an associated accessory to the patient support member, the plurality of curved surfaces being without planar portions oriented in a substantially perpendicular relation to said planar top surface of the patient support member so that first portions of an associated x-ray signal passing through the connection interface along a path substantially perpendicular to the planar top surface are attenuated substantially the same as second portions of the x-ray signal passing through the patient support member, the plurality of curved surfaces including a first connection area adjacent the planar top surface of the patient support member and a second connection area extending between the first connection area and the bottom surface of the patient support member, the first connection area including a curved lip surface and a curved recess surface formed in said planar top surface of the patient support member adjacent said curved lip surface, and the second connection area including a planar locating surface disposed in a non-perpendicular relation relative to said planar top surface.

29. The surgical table according to claim 26 wherein the planar locating surface extends at a selected angle relative to the top and bottom surfaces of the patient support member.

30. A surgical table comprising:
a base member;
a column connected with the base member;
a patient support member carried on the column, the patient support member including substantially planar top and bottom surfaces and a plurality of curved surfaces defining an accessory connection interface along at least one edge of the patient support member for selectively connecting an associated accessory to the patient support member, the plurality of curved surfaces:
being without planar portions oriented in a substantially perpendicular relation to said planar top surface of the patient support member so that first portions of an associated x-ray signal passing through the connection interface along a path substantially perpendicular to the planar top surface are attenuated substantially the same as second portions of the x-ray signal passing through the patent support member;
including a first connection area adjacent the planar top surface of the patient support member and a second connection area extending between the first connection area and the bottom surface of the patient support member, the first connection area including a curved lip surface and the second connection area including a planar locating surface disposed in a non-perpendicular relation with said planar top surface; and,
including a third connection area between said second connection and said bottom surface of the patient support member, the third connection area including a downwardly directed curved ridge extending from the bottom surface of the patient support member in a direction opposite from said curved lip surface of said first connection area.

* * * * *